US012636015B2

(12) United States Patent
Wang et al.

(10) Patent No.: US 12,636,015 B2
(45) Date of Patent: May 26, 2026

(54) OCCLUDER, OCCLUDING SYSTEM, AND KNOTTING METHOD FOR TIGHTENING ELEMENT IN OCCLUDER

(71) Applicant: HANGZHOU DINOVA EP TECHNOLOGY CO., LTD, Hangzhou (CN)

(72) Inventors: Yongsheng Wang, Hangzhou (CN); Jianglang Zhao, Hangzhou (CN); Jie Chen, Hangzhou (CN)

(73) Assignee: Hangzhou Dinova EP Technology Co., Ltd., Hangzhou (CN)

( * ) Notice: Subject to any disclaimer, the term of this patent is extended or adjusted under 35 U.S.C. 154(b) by 964 days.

(21) Appl. No.: 17/843,648

(22) Filed: Jun. 17, 2022

(65) Prior Publication Data

US 2022/0346803 A1      Nov. 3, 2022

Related U.S. Application Data

(63) Continuation of application No. PCT/CN2020/137639, filed on Dec. 18, 2020.

(30) Foreign Application Priority Data

Dec. 18, 2019   (CN) .......................... 201911313841.7
Dec. 18, 2019   (CN) .......................... 201922292918.9

(51) Int. Cl.
*A61B 17/12*           (2006.01)
(52) U.S. Cl.
CPC .. *A61B 17/12122* (2013.01); *A61B 17/12168* (2013.01)
(58) Field of Classification Search
CPC .... A61B 17/12022; A61B 2017/00606; A61B 17/12027; A61B 17/12031;
(Continued)

(56) References Cited

U.S. PATENT DOCUMENTS 4,917,089  A       4/1990  Sideris
5,284,488  A  *   2/1994  Sideris .............. A61B 17/0057
                                                    606/213
(Continued)

FOREIGN PATENT DOCUMENTS

CN          201831930  U       5/2011
CN          103654883  A       3/2014
(Continued)

OTHER PUBLICATIONS

Office Action dated Nov. 23, 2023 for corresponding European Application No. 20904197.9.

(Continued)

*Primary Examiner* — Darwin P Erezo
*Assistant Examiner* — Mitchell Brian Hoag

(57)                ABSTRACT

Disclosed is an occluder for occluding a defect in a vasculature. The occluder includes: two occluding disks and a tightening element. The two occluding disks is configured for covering different openings of the defect; wherein the tightening element includes a tightening thread, the tightening thread passing through the defect and being connected to the two occluding disks, the tightening thread has a length between the two occluding disks and the length is adjustable by means of a free end of the tightening thread. Further provided are an occluding system provided with the occluder, a knotting method for the tightening element of the occluder and a method for occluding an oval foramen with the occluder.

24 Claims, 12 Drawing Sheets

(58) Field of Classification Search
CPC ............ A61B 7/12036; A61B 17/1204; A61B
17/12045; A61B 17/12122; A61B
17/12131; A61B 17/12145; A61B
17/1215; A61B 17/12154; A61B
17/12159; A61B 17/12163; A61B
17/12168; A61B 17/12172; A61B
17/12177; A61B 17/12099; A61B
17/12104; A61B 17/12109; A61B
17/12113; A61B 17/0057; A61B
2017/00575; A61B 2017/00615; A61B
2017/00619; A61B 2017/00623; A61B
2017/00641; A61B 2017/00637; A61B
2017/00632; A61B 2017/00628
See application file for complete search history.

(56) References Cited

U.S. PATENT DOCUMENTS

| | | | | |
|---|---|---|---|---|
| 5,433,727 | A * | 7/1995 | Sideris ............... | A61B 17/0057 606/213 |
| 10,653,402 | B2 * | 5/2020 | De Rezende Neto ...................... | A61M 25/0074 |
| 2003/0158578 | A1 * | 8/2003 | Pantages ............ | A61B 17/0057 606/213 |
| 2004/0243122 | A1 * | 12/2004 | Auth .................. | A61B 18/1492 606/49 |
| 2005/0119675 | A1 * | 6/2005 | Adams ............... | A61B 17/0057 606/151 |
| 2005/0192626 | A1 * | 9/2005 | Widomski ....... | A61B 17/12186 606/213 |
| 2005/0267526 | A1 | 12/2005 | Wahr et al. | |
| 2006/0135991 | A1 * | 6/2006 | Kawaura ............ | A61B 17/0057 606/213 |
| 2007/0032796 | A1 * | 2/2007 | Chin-Chen ........ | A61B 17/0057 606/139 |
| 2007/0032821 | A1 * | 2/2007 | Chin-Chen ........ | A61B 17/0057 606/213 |
| 2007/0185530 | A1 * | 8/2007 | Chin-Chen ............ | A61B 17/08 606/213 |
| 2007/0225755 | A1 * | 9/2007 | Preinitz .............. | A61B 17/0057 606/213 |
| 2007/0250115 | A1 * | 10/2007 | Opolski ............. | A61B 17/0057 606/215 |
| 2007/0276415 | A1 * | 11/2007 | Kladakis ............ | A61B 17/0057 606/151 |
| 2010/0059062 | A1 * | 3/2010 | Koeller ................... | A61F 6/225 128/831 |
| 2011/0054492 | A1 * | 3/2011 | Clark ................. | A61B 17/0057 606/151 |
| 2017/0095256 | A1 * | 4/2017 | Lindgren ......... | A61B 17/12172 |
| 2021/0186515 | A1 * | 6/2021 | Sorajja ............. | A61B 17/12168 |
| 2022/0022935 | A1 * | 1/2022 | Sommer ................ | A61B 18/14 |

FOREIGN PATENT DOCUMENTS

| | | | | |
|---|---|---|---|---|
| CN | 106473791 | A | 3/2017 | |
| CN | 107296668 | A | 10/2017 | |
| CN | 108451570 | A | 8/2018 | |
| CN | 207837587 | U * | 9/2018 | ........ A61B 17/0057 |
| CN | 209770426 | U | 12/2019 | |
| WO | WO2008010738 | A2 | 1/2008 | |

OTHER PUBLICATIONS

International Search Report dated Mar. 17, 2021 for corresponding PCT Application No. PCT/CN2020/137639.
Written opinion dated Mar. 22, 2021 for corresponding PCT Application No. PCT/CN2020/137639.

* cited by examiner

OCCLUDER, OCCLUDING SYSTEM, AND KNOTTING METHOD FOR TIGHTENING ELEMENT IN OCCLUDER

TECHNICAL FIELD

The present disclosure relates to the field of medical instruments, and in particular to an occluder and an occluding system for occluding a defect in a human body, and a knotting method for the waist of the occluder. The occluder may be used for occluding the oval foramen and may also be used for occluding patent ductus arteriosus, an atrial septal defect, a ventricular septal defect, etc.

BACKGROUND

The human oval foramen is generally closed within one year of birth, if the oval foramen of a child over three years is still patent, it is referred to as PFO (Patent Oval Foramen). The oval foramen of 20% to 25% of adults is incompletely closed. The PFO means that a septum primum and a septum secundum on the fossa ovalis are incompletely joined, and there is a permanent fracture-like defect therebetween, thereby causing the malformation of horizontal diffluence of atria.

With the progress of science and technology and particularly the development of a catheterization technology, transcatheter interventional occluders have become an important treatment method for minimally invasive therapy of congenital heart diseases such as PFOs, atrial septal defects, ventricular septal defects and patent ductus arteriosus. The transcatheter interventional occluders serve as common medical instruments in a transcatheter interventional therapy method. Since PFOs and the atrial septal defects are different in dissection, a device for occluding the PFO is required to be necessarily improved on the basis of a device for occluding the atrial septal defect. A traditional PFO occluder includes occlusion surfaces of double-plate and cylindrical thin waists perpendicular to the occlusion surfaces of double-plate, the septum primum and the septum secundum pressed by the cylindrical thin waists and deformed, and the occlusion surfaces of double-plate clamp and fix the deformed defect to block blood from flowing therethrough.

However, the traditional PFO occluder is only suitable for treating PFO having a short overlap on the septum primum and the septum secundum, but is very difficult to play a role in occluding PFO having a long overlap therebetween, in which greater residual diffluence is readily caused between the septum primum and the septum secundum after treatment, when the blood flows through the oval foramen, the flow rate of blood will be changed which may induce the formation of thrombosis, and therefore, a long time of anticoagulant therapy is required for the patient; and if the formed thrombosis enters the blood circulation, serious adverse events such as embolism may also be caused. Moreover, the distance between occlusion surfaces of the double-plate of a traditional occluder is fixed, it is impossible to adjust the length of the waist according to the structure of the oval foramen, and thus, the occluder comply to an anatomical structure of the oval foramen.

SUMMARY

In view of this, the present disclosure provides an occluder for occluding a defect in a vasculature. The occluder includes two occluding disks and a tightening element; the two occluding disks are configured for covering different openings of the defect; and the tightening element includes a tightening thread, the tightening thread passes through the defect and is connected to the two occluding disks, the tightening thread has a length between the two occluding disks, and the length is adjustable by means of a free end of the tightening thread.

The present disclosure further provides an occluding system including an occluder and a delivery device. The occluder is configured for occluding a defect in a vasculature; the occluder includes two occluding disks and a tightening element; the two occluding disks are configured for covering different openings of the defect; and the tightening element includes a tightening thread, the tightening thread passes through the defect and is connected to the two occluding disks, the tightening thread has a length between the two occluding plates, and the length is adjustable by means of a free end of the tightening thread. The delivery device is configured for releasing the occluder.

The present disclosure further provides a knotting method for a tightening element of the occluder, wherein the tightening element is formed by twisting and knotting a thread body. The thread body includes a locking section, a first section, a second section and an adjusting section which are connected in sequence, and the knotting method includes the following steps:

forming a thread loop by winding the first section to obtain a base thread loop;

directing the remaining part of the first section to pass through the base thread loop to obtain a locking thread loop; and directing the adjusting section to pass through the locking thread loop such that the second section forms an adjusting thread loop between two occluding disks of the occluder, thereby obtaining the tightening element.

The present disclosure further provides a method of occluding an oval foramen in a heart of a patient with the occluder, wherein the two occluding disks comprises a first occluding disk and a second occluding disk, the method includes steps of:

delivering the occluder into the heart of the patient;

releasing the first occluding disk into a left atrium of the heart, and releasing the second occluding disk into a right atrium, with the tightening thread passing through the oval foramen; and adjusting the length of the tightening thread between the first occluding disk and the second occluding disk such that tissues surrounding the oval foramen is clamped by the first occluding disk and the second occluding disk.

The two occluding disks of the occluding system provided by the present disclosure respectively cover the periphery of the different openings of the defect. The distance between the two occluding disks is controlled by adjusting the length of the tightening thread between the two occluding disks, which improves the attachment of the two occluding disks to tissues surrounding the defect, and thus, the defect is stably occluded. That is, after the occluder is implanted, it is ensured that the degree of the deformation of the defect is smaller, the endothelialization of the occluding disks is not affected, residual diffluence is reduced, the trouble of requirement to customize the occluder for a particular patient due to specific structure of the defect is avoided, and the application of the occluder is effectively widened, so that more patients get benefits from minimally invasive surgeries.

BRIEF DESCRIPTION OF THE DRAWINGS

In order to illustrate the technical solutions in the embodiments of the present disclosure more clearly, the accompanying drawings that are required to be used in the implementations will be briefly introduced below. Apparently, the accompanying drawings that are described below are some implementations of the present disclosure, and those of ordinary skill in the art may obtain other accompanying drawings according to these accompanying drawings without creative work.

DESCRIPTION OF THE EMBODIMENTS

The technical solutions in the embodiments of the present disclosure will be described clearly and completely below in conjunction with accompanying drawings in the embodiments of the present disclosure. Apparently, the described embodiments are only a part of the embodiments of the present disclosure, but not all the embodiments. Based on the embodiments of the present disclosure, all other embodiments obtained by those of ordinary skill in the art without creative work fall within the protection scope of the present disclosure.

In the description of the present disclosure, it should be noted that directional or positional relationships indicated by terms such as "upper", "lower", "inner" and "outer" are directional or positional relationships based on the accompanying drawings, are merely intended to facilitate describing the present disclosure and simplifying the description, rather than to indicate or imply that the appointed device or element has to be located in a specific direction or structured and operated in the specific direction so as not to be understood as restrictions on the present disclosure. In addition, terms such as "first" and "second" are for descriptive purposes only, and cannot be understood as indicating or implying the relative importance.

In the description of the present disclosure, it should be noted that, in the field of interventional medical instruments, a proximal end refers to the end close to an operator, and a distal end refers to the end away from the operator; and an axial direction refers to a direction parallel to a connecting line between a distal-end center and a proximal-end center of a medical instrument in a natural state. The abovementioned definitions are only for convenience of descriptions, but may not be understood as limitations to the present disclosure.

Figure 1:
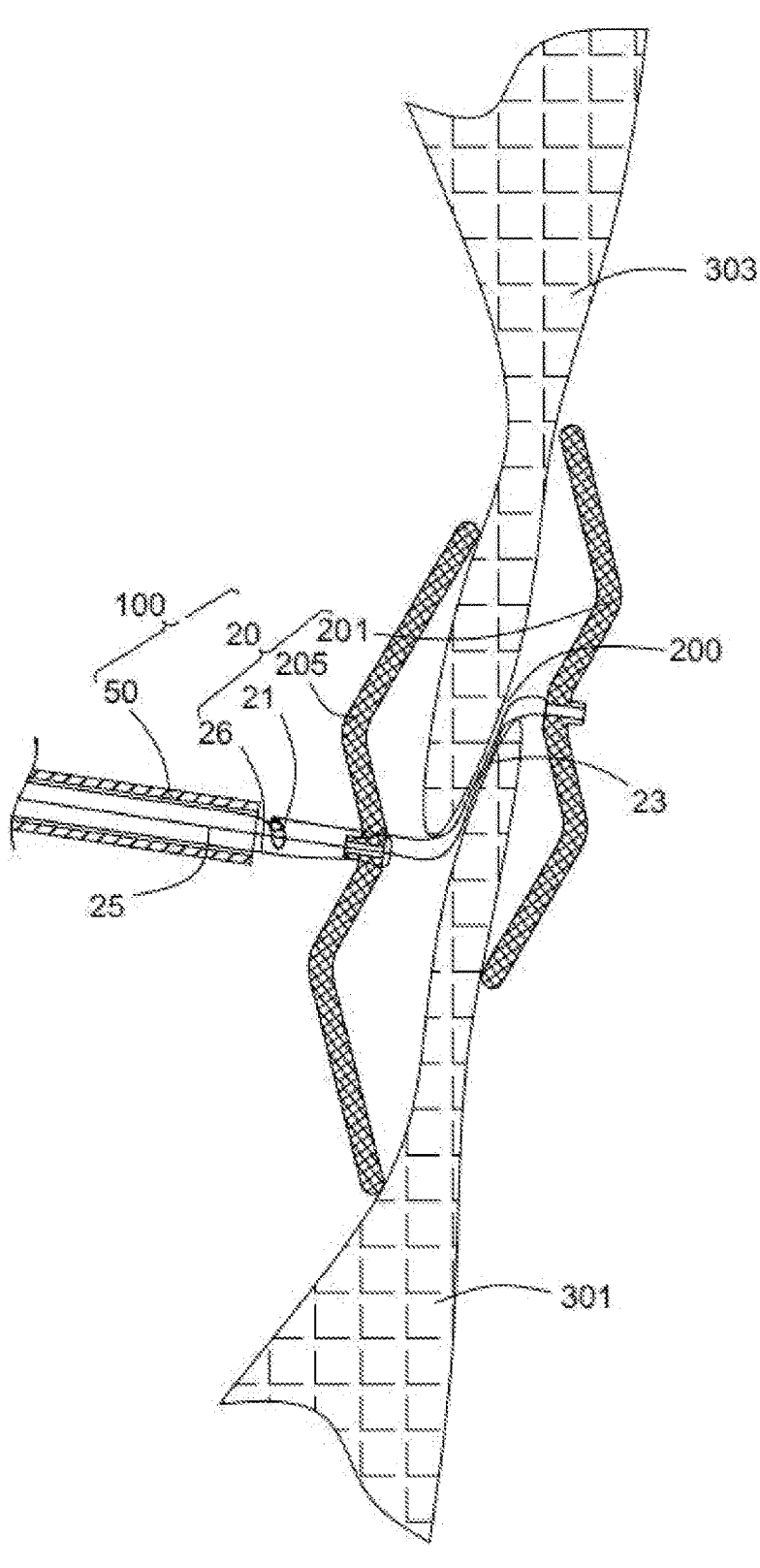
FIG. 1 is a schematic structural view of an occluding system according to a first embodiment of the present disclosure during release.
Figure 2:
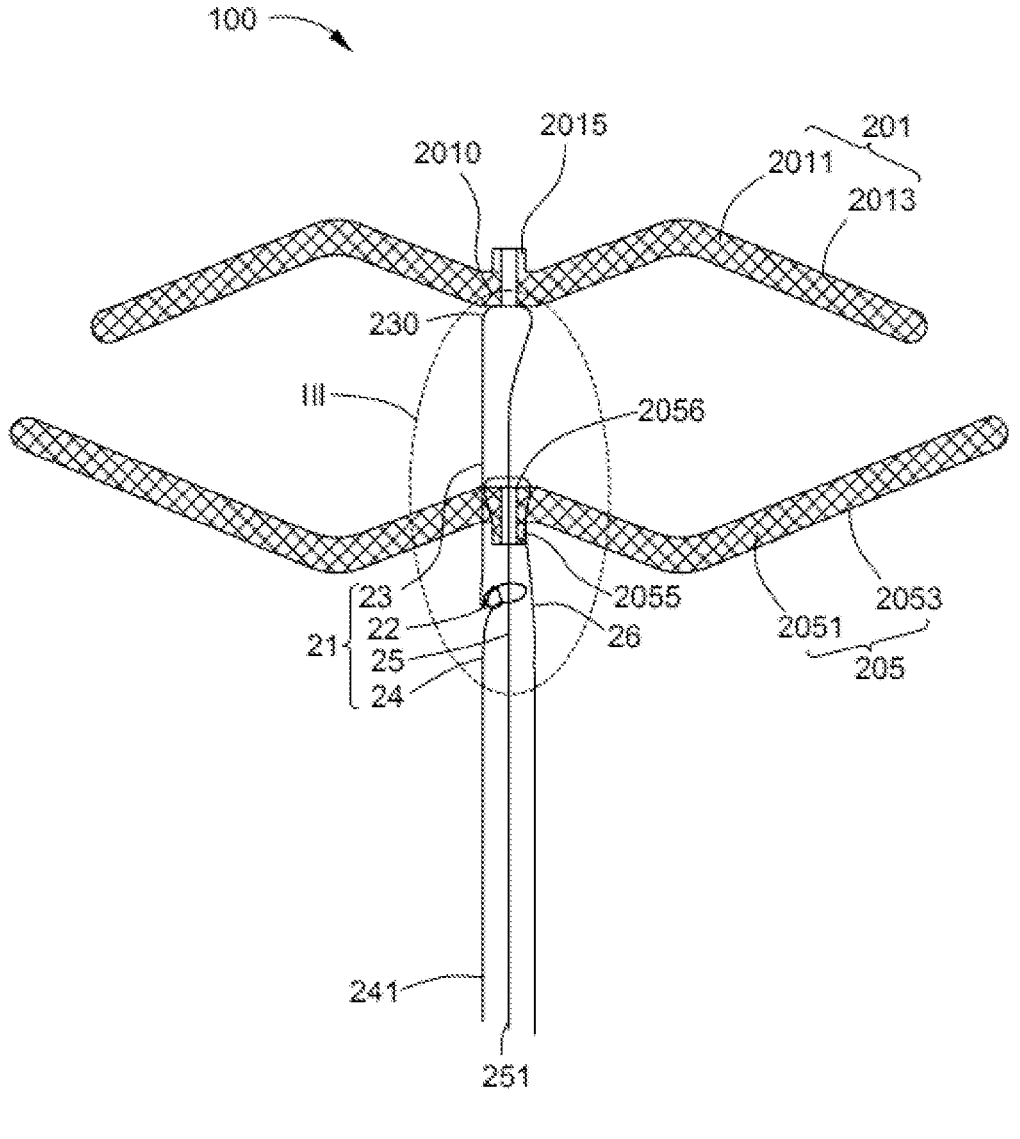
FIG. 2 is an enlarged view of the occluding system shown in FIG. 1.
Figure 3:
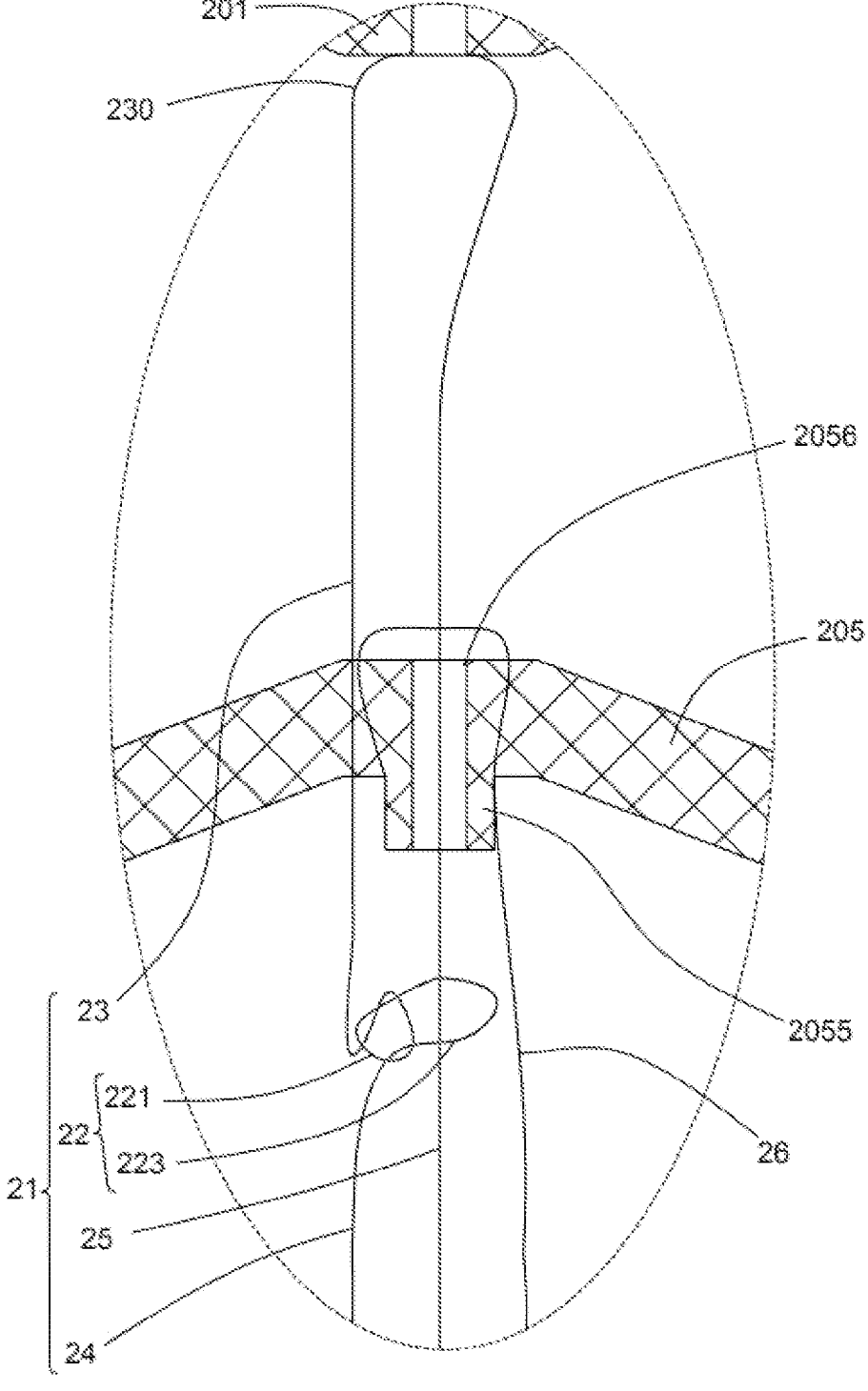
FIG. 3 is an enlarged view of a portion III shown in FIG. 2.

Reference is made to FIG. 1 to FIG. 3, the present disclosure provides an occluding system 100 including an occluder 20 and a delivery device 50 for releasing the occluder 20. The occluder 20 is used for occluding a defect in a vasculature, and the defect includes, but is not limited to an oval foramen, ductus arteriosus, an atrial septal defect and a ventricular septal defect. In the present disclosure, the oval foramen 200 will be taken as the example of the defect, to illustrate the advantages of the occluding system 100 for treating the PFOs. It may be understood that the defect may also be other defects as mentioned above.

The occluder 20 includes two occluding disks and a tightening element. The two occluding disks are used for covering different openings of the oval foramen 200, which are the two openings of the oval foramen 200 respectively located in the left atrium and the right atrium. The tightening element includes a tightening thread 21, and the tightening thread is formed by twisting and knotting a thread body. The tightening thread 21 passes through the oval foramen 200 and is connected to the two occluding disks. The length of the tightening thread 21 located between the two occluding disks is adjustable by means of a free end of the tightening thread 21.

After the occluding system 100 according to the present disclosure is implanted into a human body, the two occluding disks respectively cover the peripheries of the two opposite side openings of the oval foramen 200, that is, regions on two side surfaces of both of a septum primum 301 and a septum secundum 303 adjacent to the oval foramen 200 are covered by the two occluding disks. By adjusting the length of the tightening thread 21 between the two occluding disks, the distance of the two occluding disks is controlled so as to adapt to an anatomical structure of a patient, which improves the attachment of the two occluding disks to the oval foramen 200, and thus, the oval foramen 200 is stably occluded. After the occluder 20 is implanted, it is ensured that the degree of the deformation of two septa (the septum primum 301 and the septum secundum 303) is smaller, the endothelialization of the two septa to the occluding disks is not affected, residual diffluence is reduced, the trouble of requirement to customize the occluder for a particular patient due to a specific structure of the oval foramen 200 is avoided, and the application of the PFO occluder is effectively widened, so that more patients get benefits from minimally invasive surgeries.

In case that the defect has two or more openings, the occluder 20 is further used for occluding a plurality of openings in the defect from two sides.

As shown in FIG. 2 and FIG. 3, the two occluding disks are respectively a first occluding disk 201 and a second occluding disk 205. The tightening thread 21 includes a knot 22, a connecting section 23 connected with the knot 22, as well as a locking section 24 and an adjusting section 25 which are connected with the knot 22. The connecting section 23 is connected between the first occluding disk 201 and the second occluding disk 205. Preferably, the connecting section 23 is connected to the geometric center of the first occluding disk 201, and/or the connecting section 23 is connected to the geometric center of the second occluding disk 205. The locking section 24 includes a free end 241. The adjusting section 25 includes a free end 251. All of the locking section 24, the adjusting section 25 and the knot 22 are disposed on one side of the second occluding disk 205 away from the first occluding disk 201. The length of the connecting section 23 can be adjusted by means of the adjusting section 25. The free end 241 of the locking section 24 and the free end 251 of the adjusting section 25 are connected to the delivery device 50. The delivery device 50 is controllable to pull the free end 251 so as to adjust the length of the connecting section 23 between the first occluding disk 201 and the second occluding disk 205, thereby adjusting the distance between the two occluding disks. The delivery device 50 is controllable to pull the free end 241 to lock the adjusting section 25 by the knot 22, so that the distance between the first occluding disk 201 and the second occluding disk 205 is fixed relative to each other, to thereby fix the distance between the first occluding disk 201 and the second occluding disk 205, which is advantageous to maintain the relative positions of the septum primum 301, the septum secundum 303 and the two occluding disks and attachment there during and after the operation, and thus, the difficulty in withdrawing the delivery device 50 is reduced, and it facilitates to growth of the two septa towards the occluder 20 to complete endothelialization and form a permanent atrial septa after operation.

As shown in FIG. 2, both of the adjusting section 25 and the locking section 24 are movable threads connected to the occluding disks, operating the adjusting section 25 or the locking section 24 independently may cause the occluding disks to move, and thus, unsatisfied operability may be caused. Therefore, the tightening element further includes a fixing thread 26 connected with the delivery device 50. One of the two occluding disks is fixed, by means of the fixing thread 26, to a distal end of the delivery device 50. Specifically, the second occluding disk 205 is connected with the fixing thread 26, and the fixing thread 26 is used for fixing the second occluding disk 205 to the distal end of the delivery device 50 to prevent both of the two occluding disks from shaking when the adjusting section 25 or the locking section 24 is pulled, thereby facilitating to adjust the length of the connecting section 23 and lock the adjusting section 25 by the knot 22. In the present embodiment, one end of the fixing thread 26 is connected to a central portion of the second occluding disk 205, and the other end of the fixing thread 26 is fixed to the delivery device 50.

As shown in FIG. 1, in the present embodiment, during use, the first occluding disk 201 is delivered to the left atrium by the delivery device 50 and is unfolded in the left atrium, and the second occluding disk 205 is delivered to the right atrium by the delivery device 50 and is unfolded in the right atrium. The connecting section 23 connected between the first occluding disk 201 and the second occluding disk 205 is flexible and is adjustable in length. The connecting section 23 passes through the oval foramen 200 between the septum primum 301 and the septum secundum 303. The adjusting section 25 is pulled towards the proximal end to shorten the connecting section 23 gradually, that is, the distance between the first occluding disk 201 and the second occluding disk 205 is gradually reduced. The septum primum 301 and the septum secundum 303 approach each other and are clamped by the first occluding disk 201 and the second occluding disk 205. The first occluding disk 201 covers the septum primum 301 and the septum secundum 303 at areas around the oval foramen 200, and the second occluding disk 205 covers the septum primum 301 and the septum secundum 303 at areas around the oval foramen 200, that is, the two side openings of the oval foramen 200 in the left atrium and the right atrium are respectively covered by the first occluding disk 201 and the second occluding disk 205. In the present embodiment, each of the first occluding disk 201 and the second occluding disk 205 includes a supporting frame and a flow blocking membrane disposed on the supporting frame. The flow blocking membranes on two sides of the oval foramen 200 can block blood to flow into the oval foramen 200, thereby preventing a blood flow from flowing from the left atrium to the right atrium and thus achieving occlusion immediately. After the occluder 20 is implanted to a human body, the septum primum 301 and the septum secundum 303 creep to positions where they are in contact with the first occluding disk 201 and the second occluding disk 205, respectively, so that the oval foramen 200 is closed after endothelialization is completed, and then, an integrated atrial septum can be formed. In an alternative embodiment, structures of the supporting frames on the two occluding disks are dense enough, as such the flow blocking membranes can be omitted, which will not affect the endothelialization of the two septa to the occluding disks, and no diffluence or little diffluence will be formed on a passageway of the oval foramen, for example, the diffluence is less than a preset proportion which may be 10%, 5%, 3%, etc.

The faces of the first occluding disk 201 and the second occluding disk 205 may be configured to be circular, oval, triangular or of other shapes which are irregular. The radial area of the first occluding disk 201 may be the same as or different from the radial area of the second occluding disk 205. In the present embodiment, both of the first occluding disk 201 and the second occluding disk 205 are substantially plate-shaped, and the radial area of the first occluding disk 201 is smaller than the radial area of the second occluding disk 205.

Specifically, as shown in FIG. 2, the first occluding disk 201 includes a first supporting frame 2011 and a first flow blocking membrane 2013 disposed on the first supporting frame 2011. The first flow blocking membrane 2013 may be fixedly attached to the inner surface and/or outer surface of the first supporting frame 2011. the first flow blocking membrane 2013 may alternatively be fixedly disposed in an inner cavity of the first supporting frame 2011, and the first flow blocking membrane 2013 at least covers a radial region of the first supporting frame 2011. The tightening thread 21 is connected with the first supporting frame 2011 and/or the first flow blocking membrane 2013. In the present embodiment, the connecting section 23 of the tightening thread 21 slidably passes through the first supporting frame 2011.

The second occluding disk 205 includes a second supporting frame 2051 and a second flow blocking membrane 2053 disposed on the second supporting frame 2051. The second flow blocking membrane 2053 may be fixedly attached to the inner surface and/or outer surface of the second supporting frame 2051. The second flow blocking membrane 2053 may alternatively be fixedly disposed in an inner cavity of the second supporting frame 2051, and the second flow blocking membrane 2053 at least covers a radial region of the second supporting frame 2051. One end of the adjusting section 25 passes through the second flow blocking membrane 2053 from a gap in the second supporting frame 2051, so as to be connected with the knot 22.

The first flow blocking membrane 2013 and the second flow blocking membrane 2053 may be membranes made of non-degradable polymer materials having good biocompatibility, such as ePTFE or PET materials. The first flow blocking membrane 2013 and the second flow blocking membrane 2053 may alternatively be made of absorbable polymer materials such as polylactic acid, polycaprolactone, polylactic acid-polycaprolactone copolymer and the like. The first flow blocking membrane 2013 and the second flow blocking membrane 2053 are fixed to the inner or outer surfaces of the occluding disks by means of suturing or adhering to occlude the blood flow. In the present embodiment, the outer surface of the first occluding disk 201 is fixedly attached with the first flow blocking membrane 2013. The outer surface of the second occluding disk 205 is fixedly attached with the second flow blocking membrane 2053.

The first supporting frame 2011 and the second supporting frame 2051 are woven meshed structures or cut frame structures, so that the first occluding disk 201 and the second occluding disk 205 may be sufficiently attached to the surface of the atrial septum. Each of the first supporting frame 2011 and the second supporting frame 2051 may be anyone of the following: a single-layer woven meshed structure, a single-layer cut frame structure, a double-layer meshed structure and a double-layer cut frame structure. In the present embodiment, both of the first supporting frame 2011 and the second supporting frame 2051 are single-layer woven meshed structure.

The woven meshed structures or cut frame structures may have a petal-like shape, that is, the first supporting frame 2011 and the second supporting frame 2051 are of the petal-shaped structures. The petal-shaped structure consists of a plurality of supporting wire units, which are arranged in an annular array around a center of the woven meshed structure or cut frame structure. Each of the supporting wire units passes through the center. The first supporting frame

2011 and the second supporting frame 2051 may be made of various biocompatible materials, that is, each of the supporting wire units may be made of various biocompatible materials, and the various biocompatible materials include materials commonly used in the manufacture of an implantable medical instrument, such as memory alloy materials, preferably, nickel-titanium alloy. The first supporting frame 2011 and the second supporting frame 2051 may alternatively be made of degradable materials, that is, each of the supporting wire units is made of the degradable material, and the degradable materials include polylactic acid (PLA), polycaprolactone (PCL), polyglycollide (PGA), and polydioxanone (PDO) and the like. Alternatively, the supporting frames may be made of macromolecular polymer materials, etc.

In the present embodiment, the peripheral edge of the first supporting frame 2011 is inclinedly bent towards the second supporting frame 2051, and the peripheral edge of the second supporting frame 2051 is inclinedly bent towards the first supporting frame 2011. Specifically, the portion of each supporting wire unit of the first supporting frame 2011 away from the geometric center of the first supporting frame 2011 is inclinedly bent towards the second supporting frame 2051. The portion of each supporting wire unit of the second supporting frame 2051 away from the geometric center of the second supporting frame 2051 is inclinedly bent towards the first supporting frame 2011. When tissues surrounding the oval foramen 200 are clamped together by the first occluding disk 201 and the second occluding disk 205, the distance between the central portions of the first occluding disk 201 and the middle of the second occluding disk 205 is greater than the distance between the peripheral edges thereof, so that the septum primum 301 and the septum secundum 303 surrounding the oval foramen may be more firmly clamped by the first occluding disk 201 and the second occluding disk 205.

Figure 4:
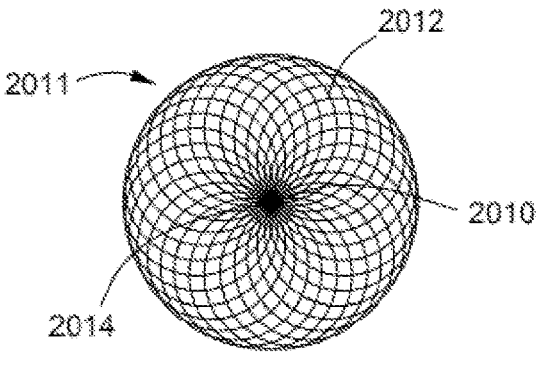
FIG. 4 is a schematic structural view of a supporting frame of an occluder according to the first embodiment of the present disclosure.

As shown in FIG. 2, FIG. 3 and FIG. 4, the first occluding disk 201 further includes a first rigid sleeve 2015 disposed in a central region thereof. Preferably, the first rigid sleeve 2015 is disposed in the geometric center of the first occluding disk 201. The supporting wire units 2012 of the first occluding disk 201 are connected with the first rigid sleeve 2015 and are disposed around the first rigid sleeve 2015 to form the first supporting frame 2011. The first rigid sleeve 2015 is tubular and is provided with a through hole extending in a thickness direction (a direction perpendicular to the surface of the first occluding disk 201) of the first occluding disk 2011. Free ends of the supporting wire units 2012 are fixedly disposed on the outer or inner circumferential surface of the first rigid sleeve 2015. In the present embodiment, the free ends of the supporting wire units 2012 are accommodated in an inner cavity of the first rigid sleeve 2015 and are fixedly connected to the first rigid sleeve 2015 by welding or bonding. The first rigid sleeve 2015 is made of stainless steel, nickel-titanium alloy or other biocompatible materials.

The second occluding disk 205 further includes a second rigid sleeve 2055 disposed in a central region thereof. The second rigid sleeve 2055 is connected with the second supporting frame 2051. Preferably, the second rigid sleeve 2055 is fixedly disposed in the geometric center of the second occluding disk 205. The supporting wire units of the second occluding disk 205 are disposed around the second rigid sleeve 2055 to form the second supporting frame 2051. The second rigid sleeve 2055 is tubular and is provided with a through threading hole 2056 in a thickness direction of the second supporting frame 2051. One end of the connecting section 23 passes through the threading hole 2056 so as to be connected with the knot 22. Free ends of the supporting wire units are fixedly disposed on the outer or inner peripheral surface of the second rigid sleeve 2055. In the present embodiment, the free ends of the several supporting wire units are fixedly connected to the outer peripheral surface of the second rigid sleeve 2055 by welding or bonding. The second rigid sleeve 2055 is made of stainless steel, nickel-titanium alloy or other biocompatible materials.

In other embodiments, the first rigid sleeve 2015 may also be disposed in a region of the first occluding disk 201 other than the central region thereof. The second rigid sleeve 2055 may also be disposed in a region of the second occluding disk 205 other than the central region thereof.

Figure 5:
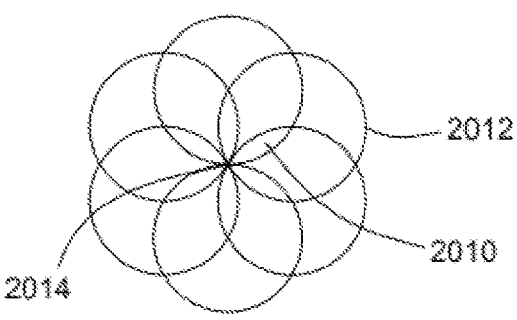
FIG. 5 is an alternative schematic structural view of a supporting frame of the occluder according to the first embodiment of the present disclosure.
Figure 6:
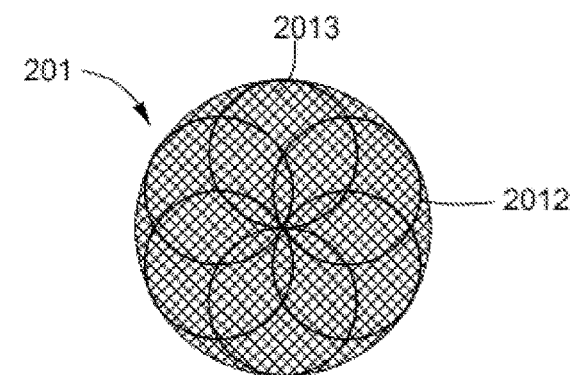
FIG. 6 is a schematic structural view showing a flow blocking membrane is disposed on the supporting frame in FIG. 5.

In other embodiments, the first supporting frame 2011 and the second supporting frame 2051 are generally woven by using 4 to 50 supporting wire units, with mesh openings defined between the adjacent supporting wire units. In the following, the first supporting frame 2011 will be taken as example for illustration, and the following technical solution is also suitable for the second supporting frame 2051. The first supporting frame 2011 shown in FIG. 4 is formed by thirty circular supporting wire units 2012 annularly arranged in array. The first supporting frame 2011 shown in FIG. 5 and FIG. 6 is formed by six circular supporting wire units 2012 annularly arranged in array. The first supporting frame 2011 shown in FIG. 6 is provided with a first flow blocking membrane 2013.

Figure 7:
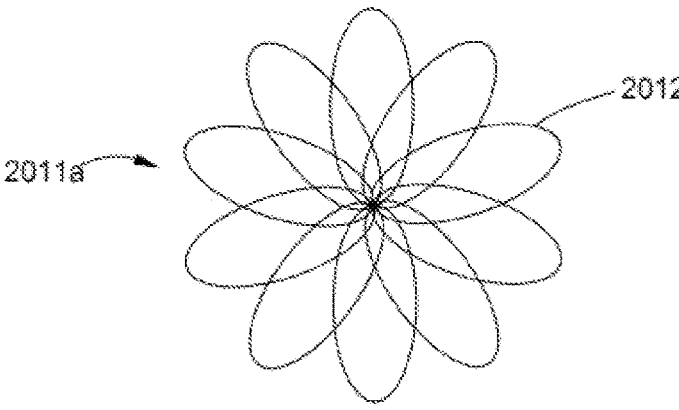
FIG. 7 is an alternative schematic structural view of a supporting frame of the occluder according to the first embodiment of the present disclosure.
Figure 8:
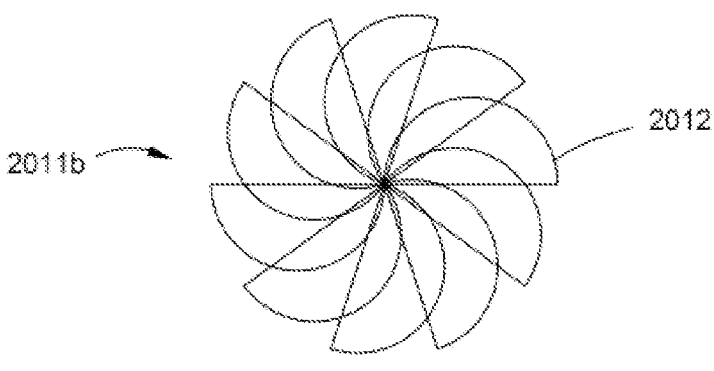
FIG. 8 is an alternative schematic structural view of a supporting frame of the occluder according to the first embodiment of the present disclosure.
Figure 9:
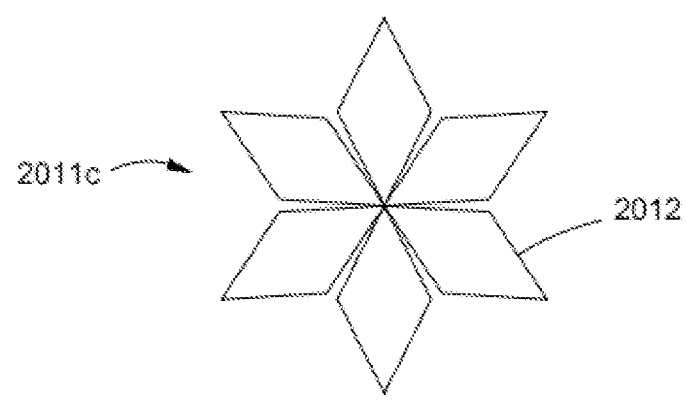
FIG. 9 is an alternative schematic structural view of a supporting frame of the occluder provided in the first embodiment of the present disclosure.
Figure 10:
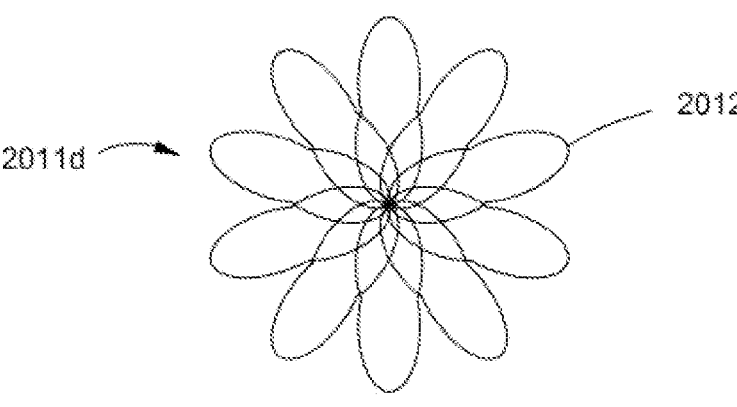
FIG. 10 is an alternative schematic structural view of a supporting frame of the occluder according to the first embodiment of the present disclosure.

In other embodiments, each of the supporting wire units may be oval, semicircular, rhombic or irregular shapes. As shown in FIG. 7, a first supporting frame 2011a is formed by a plurality of oval supporting wire units 2012 annularly arranged in array around a central point of the first supporting frame 2011a. One vertex of each supporting wire unit 2012 passes through the central point. The inner surface and/or the outer surface of the first supporting frame 2011a is provided with the flow blocking membrane. As shown in FIG. 8, a first supporting frame 2011b is formed by a plurality of semicircular supporting wire units 2012 annularly arranged in array around a central point of the first supporting frame 2011b. One end of the arc of each supporting wire unit 2012 passes through the central point. The inner surface and/or the outer surface of the first supporting frame 2011b is provided with the flow blocking membrane. As shown in FIG. 9, a first supporting frame 2011c is formed by a plurality of rhombic supporting wire units 2012 annularly arranged in array around a central point of the first supporting frame 2011c. One vertex of each supporting wire unit 2012 passes through the central point. The inner surface and/or the outer surface of the first supporting frame 2011c is provided with the flow blocking membrane. As shown in FIG. 10, a first supporting frame 2011d is formed by a plurality of supporting wire units 2012 of the irregular shapes annularly arranged in array around a central point of the first supporting frame 2011d, a top end of each supporting wire units 2012 passes through the central point. The inner surface and/or the outer surface of the first supporting frame 2011d is provided with the flow blocking membrane.

In other embodiments, each of the supporting wire units may be triangular, polygonal, etc.

The tightening thread 21 may be a non-absorbable biocompatible suture such as a metal thread, a cotton thread, a polyester thread, a polypropylene thread, etc. The tightening thread 21 may also be an absorbable biocompatible suture such as a catgut, a polyglycollide thread, a multi-silk non-biodegradable suture, etc. The tightening thread 21 may also be a forcedly-wound fiber thread, etc.

Reference is made to FIG. 2 and FIG. 3 again, the locking section 24 and the adjusting section 25 are respectively located on two ends of the connecting section 23, and the knot 22 is located between the connecting section 23 and the locking section 24. The connecting section 23 is an inverted U-shaped adjusting thread loop 230 defined by the thread body. Two ends of the adjusting thread loop 230 pass through the second occluding disk 205 and are connected with the knot 22. The part of the adjusting thread loop 230 away from the knot 22 slidably passes through the first occluding disk 201. Preferably, the part of the adjusting thread loop 230 away from the knot 22 and the adjusting section 25 slidably passes through the geometric center of the first occluding disk 201. Two ends of the adjusting thread loop 230 respectively pass through the geometric center of the second occluding disk 205 in the thickness direction of the second occluding disk 205, so that forces applied on the first occluding disk 201 and the second occluding disk 205 are more uniform. Specifically, the part of the adjusting thread loop 230 away from the knot 22 and the adjusting section 25 slidably passes through the first occluding disk 201, and two ends of the adjusting thread loop 230 respectively pass through the mesh opening in the geometric center of the second occluding disk 205, and preferably, two ends of the adjusting thread loop 230 respectively pass through different mesh openings in the second occluding disk 205, thereby facilitating connecting different components of the delivery device 50. One end of the adjusting thread loop 230 passes through the second rigid sleeve 2055 and the other end of the adjusting thread loop 230 passes through gaps between the wire units 2012 of the second supporting frame 2051. In other embodiments, two ends of the adjusting thread loop 230 respectively pass through different lumens in the second rigid sleeve 2055, or two ends of the adjusting thread loop 230 respectively pass through two different gaps between the wire units 2012 of the second supporting frame 2051.

Positions of the first occluding disk 201 and the second occluding disk 205 through which two ends of the adjusting thread loop 230 pass are located in the geometric centers of the first occluding disk 201 and the second occluding disk 205. As such, it facilitates to apply a pulling force to the geometric centers of the occluding disks when the tightening thread 21 is tightened, so that the force applied on the occluding disks is uniform, and it is convenient to operate.

Preferably, the first occluding disk 201 is connected with the connecting section 23 at a plurality of positions that are close to each other, and/or the second occluding disk 205 is connected with the connecting section 23 at a plurality of positions that are close to each other. Specifically, positions of two mesh openings of the first occluding disk 201 through which the connecting section 23 passes are close to each other. At the second occluding disk 205, one end of the connecting section 23 passes through the threading hole 2056 of the second rigid sleeve 2055, and the other end of the connecting section 23 passes through a mesh opening which is close to the threading hole 2056.

If a span between positions where two ends of the connecting section 23 pass through the flow blocking membranes on the first occluding disk 201 or/and the second occluding disk 205 is relatively large, through holes in the flow blocking membranes for the connecting section 23 to pass through are easily become larger and larger due to pulling obliquely by the connecting section 23, thereby affecting the flow-blocking effect of the flow blocking membranes. If the through holes for the connecting section 23 to pass through are too large, the positions at the through holes will not be endothelialized subsequently, which causes a poor effect on closing the oval foramen. Therefore, the positions of the through holes of the connecting section 23 on the two disks are gathered, avoiding the through holes in the flow blocking membranes from becoming larger and larger due to pulling by the connecting section 23, which facilitates to maintain the integrity of the flow blocking membranes for a long term, and it is ensured that the defected septum primum 301 and the septum secundum 303 creep towards the surface of the occluder to complete endothelialization after the operation.

One end of the adjusting thread loop 230 is connected to the knot 22, and the other end of the adjusting thread loop 230 passes through the knot 22 and is connected with the adjusting section 25. When the knot 22 is not tightened, the adjusting section 25 is capable of driving the end of the adjusting thread loop 230 connected thereto to slide in the knot 22, to thereby adjust the length of the adjusting thread loop 230 between the first occluding disk 201 and the second occluding disk 205. The locking section 24 is used for tightening the knot 22 to make the knot 22 tighten a part of the adjusting thread loop 230 located in the knot 22, to thereby fix the length of the adjusting thread loop 230 between the first occluding disk 201 and the second occluding disk 205.

As shown in FIG. 3, the knot 22 includes a base thread loop 221 and a locking thread loop 223 which are interconnected. One end of the adjusting thread loop 230 is connected with the base thread loop 221, and the other end of the adjusting thread loop 230 passes through the locking thread loop 223 and is connected with the adjusting section 25. When the base thread loop 221 and the locking thread loop 223 are not tightened, the adjusting section 25 is capable of driving the end of the adjusting thread loop 230 connected thereto to slide in the locking thread loop 223, so as to adjust the length of the adjusting thread loop 230 between the first occluding disk 201 and the second occluding disk 205. When the locking section 24 is tightened, the locking thread loop 223 and the base thread loop 221 are sequentially and gradually tightened, so that one part of the adjusting thread loop 230 is tightened and locked in the locking thread loop 223.

Figure 11:
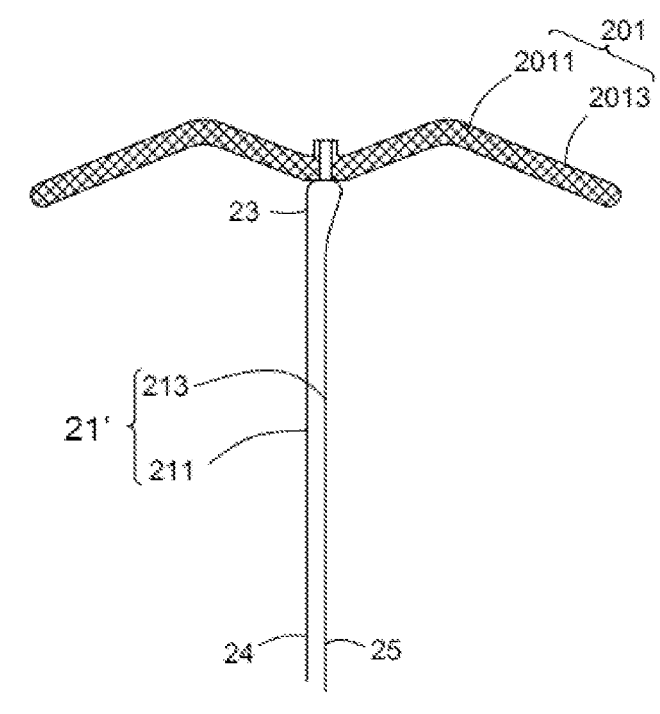
FIG. 11 is a schematic view illustrating a procedure of an assembling process of occluding disks and a tightening element of the occluder according to the first embodiment of the present disclosure.

The tightening thread 21 is formed by twisting and knotting a thread body 21'. As shown in FIG. 11, the thread body 21' includes a first section 211, a second section 213, the locking section 24 connected to the first section 211, and the adjusting section 25 connected to the second section 213. The first section 211 and the second section 213 are interconnected. The knot 22 is formed by the first section 211. Specifically, the base thread loop 221 is defined by the first section 211, and the locking thread loop 223 is formed by a remaining part of the first section 211 passing through the base thread loop 221. The adjusting thread loop 230 is defined by the second section 213.

It is defined in the present disclosure that: the sides located between the first occluding disk 201 and the second occluding disk 205 are inner sides, the side of the first occluding disk 201 away from the second occluding disk 205 is an outer side, and the side of the second occluding disk 205 away from the first occluding disk 201 is an outer side. Two ends of the adjusting thread loop 230 pass through the second occluding disk 205 from the inner side of the second occluding disk 205 to the outer side of the second occluding disk 205, and the end of the adjusting thread loop 230 away from the knot 22 passes through the inner side of the first occluding disk 201.

Reference is made to FIG. 11 to FIG. 15, a process to assemble the tightening thread 21 as well as the first occluding disk 201 and the second occluding disk 205 to a whole is described as follows.

1. As shown in FIG. 11, one end of the thread body passes through the different mesh openings of the first occluding disk 201, such as two radially-spaced mesh openings in the geometric center of the inner side of the first occluding disk 201, and then returns to the inner side of the first occluding disk 201, that is, it is close to the other end of the thread body, so that the part of the thread body away from the other end slidably passes through the first occluding disk 201. At the moment, the thread body is inverted U-shaped, the first section 211 and the second section 213 of the thread body are respectively located on two sides of an axial axis of the first occluding disk 201. One end of the first section 211 away from the first occluding disk 201 is connected with the locking section 24, and one end of the second section away from the first occluding disk 201 is connected with the adjusting section 25.

Figure 12:
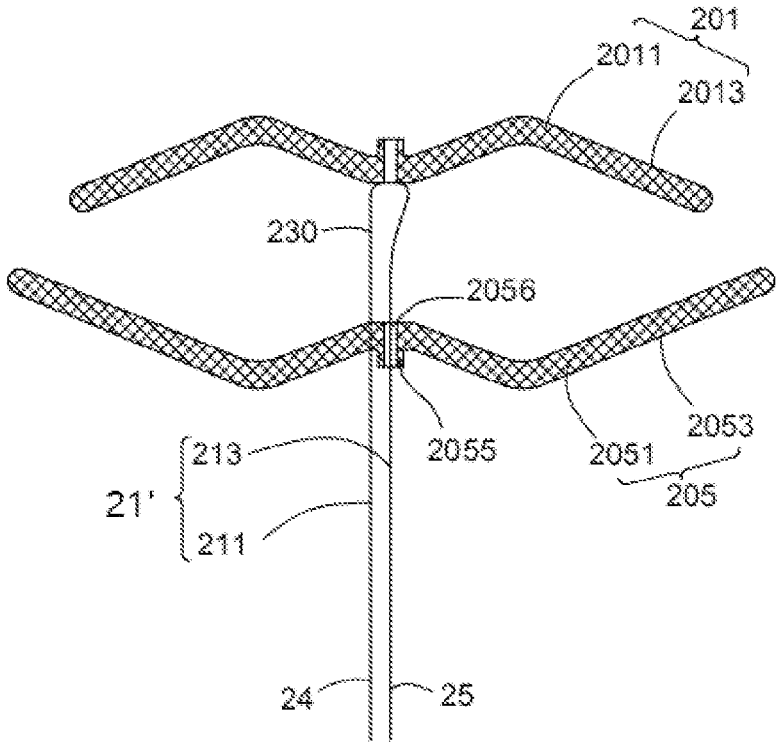
FIG. 12 is a schematic view illustrating another procedure of the assembling process of occluding disks and a tightening element of the occluder according to the first embodiment of the present disclosure.

2. As shown in FIG. 12, the adjusting section 25 passes through the threading hole 2056 of the second rigid sleeve 2055 from the inner side to the outer side of the second occluding disk 205, and the locking section 24 passes through a mesh opening in the supporting frames adjacent to the second rigid sleeve 2055 from the inner side to the outer side of the second occluding disk 205, so that the free ends of the adjusting section 25 and the locking section 24 are arranged side by side on the outer side of the second occluding disk 205. The part of the thread body located between the first occluding disk 201 and the second occluding disk 205 forms the adjusting thread loop 230.

Figure 13:
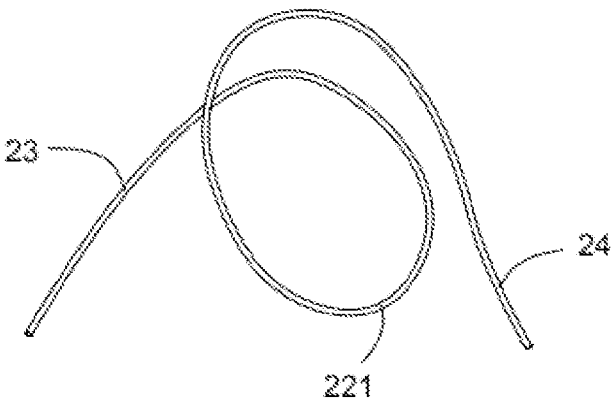
FIG. 13 is a schematic view illustrating another procedure of the assembling process of occluding disks and a tightening element of the occluder according to the first embodiment of the present disclosure.
Figure 14:
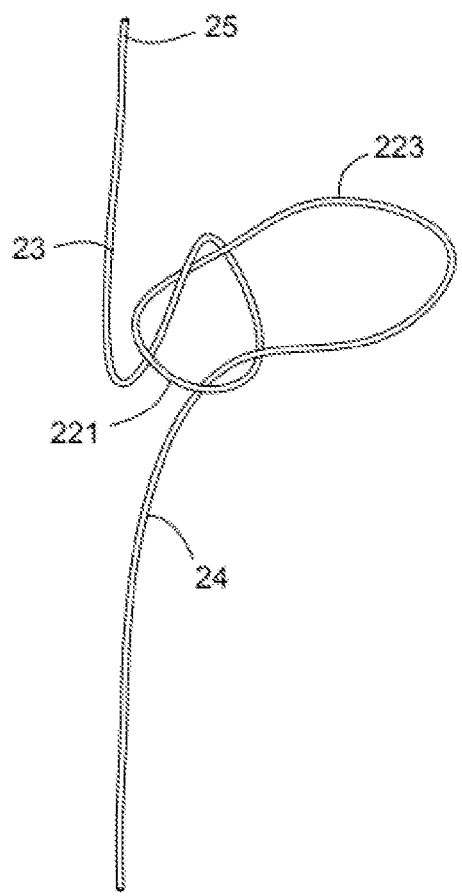
FIG. 14 is a schematic view illustrating another procedure of the assembling process of occluding disks and a tightening element of the occluder according to the first embodiment of the present disclosure.
Figure 15:
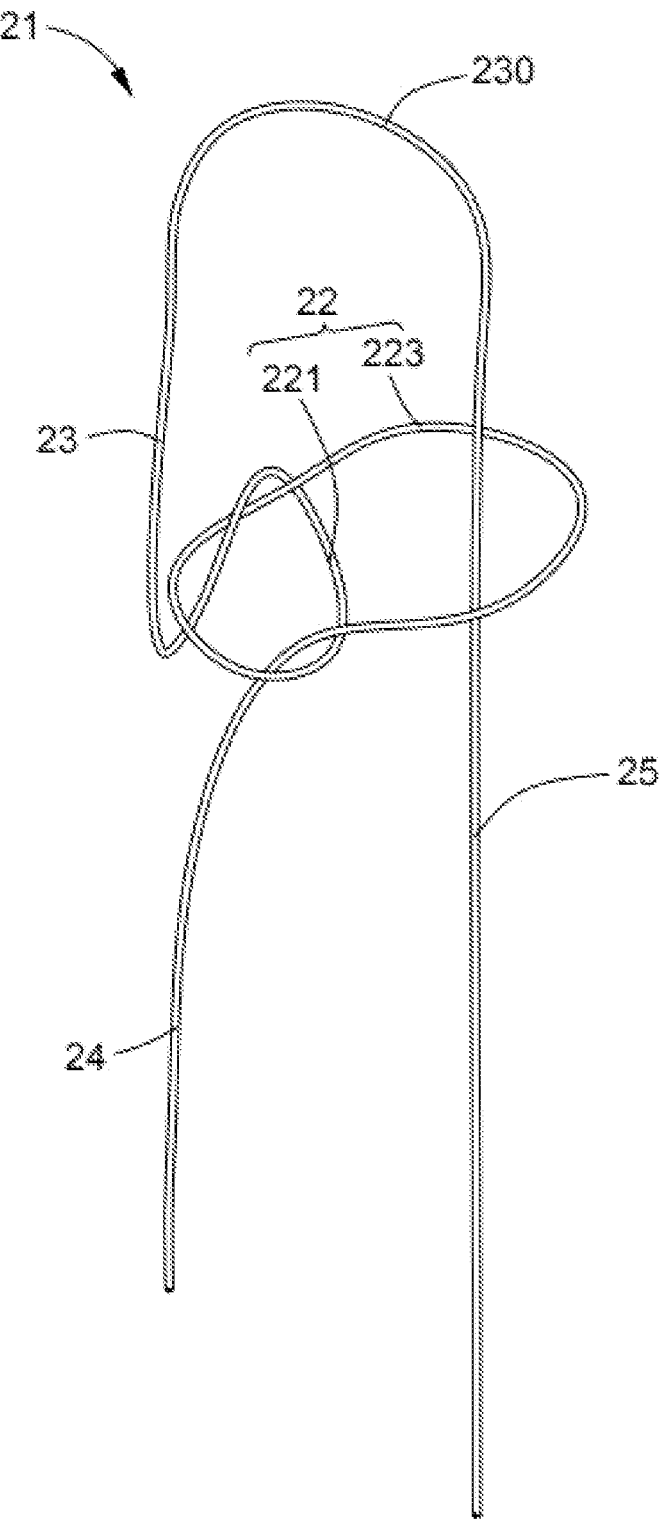
FIG. 15 is a schematic view illustrating another procedure of the assembling process of occluding disks and a tightening element of the occluder according to the first embodiment of the present disclosure.

3. As shown in FIG. 13 to FIG. 15, the tightening thread 21 is provided with the knot 22, which is formed by twisting the first section 211 and the second section 213, on the outer side of the second occluding disk 205. The knot 22 is capable of locking the locking section 24 and the adjusting section 25 and is abutted against the outer side of the second occluding disk 205 to fix the length of the adjusting thread loop 230. In the present embodiment, a knotting method for the knot 22 formed by twisting the first section 211 is described in detail as follows.

A. as shown in FIG. 13, forming a thread loop by the first section to obtain a base thread loop 221; specifically, forming a thread loop by overlapping two parts of the first section of the thread body, thereby obtaining the base thread loop 221;

B. as shown in FIG. 14, directing a remaining part of the first section to pass through the base thread loop 221 to obtain a locking thread loop 223, wherein the remaining part of the first section is connected with the locking section 24, the remaining part of the first section is wound from one side (for example, an outward side of the plane where FIG. 14 locates) of the base thread loop 221 to the other side (for example an inward side of the plane where FIG. 14 locates) of the base thread loop 221, and then passes through the base thread loop 221 from the other side of the base thread loop 221 to the side of the base thread loop 221 to obtain a U-shaped locking thread loop 223, and the locking section 24 is kept out of the base thread loop 221; and C. as shown in FIG. 15, directing the adjusting section 25 to pass through the locking thread loop 223 to ensure that the second section forms an adjusting thread loop 230 between the first occluding disk 201 and the second occluding disk 205 of the occluder, thereby obtaining the tightening thread 21.

A method of occluding a defect, such as an oval foramen, of a patient with the occluder 100 according to the present disclosure is also provided. In the following, a surgical process of occluding an oval foramen will be taken as an example for illustration.

The method of occluding an oval foramen in a heart of a patient with the occluder 100 according to the present disclosure includes:

S1. delivering the occluder 100 into the heart of the patient.

In step S1, the occluder 100 provided by the present disclosure may be used in combination with a guide wire, a delivery device 50, a dilator, etc. The step S1 may specifically include the following steps:

S11. guiding the guide wire into the left superior pulmonary vein and maintaining it there, deploying a delivery sheath and the dilator into the middle of the left atrium, and then withdrawing the dilator and the guide wire; and S12. keeping the delivery sheath stationary, inserting a delivery rod of a delivery device 50 which is loaded with the first occluding disk 201 and the second occluding disk 205 into the delivery sheath from a proximal end thereof, and then pushing the delivery rod distally, to push the distal end of the delivery rod out of the delivery sheath first.

According to the present disclosure, the method of occluding an oval foramen further includes:

S2. releasing the first occluding disk into a left atrium of the heart, and releasing the second occluding disk into a right atrium, with the tightening thread passing through the oval foramen.

The step S2 may specifically include the following steps:

S21. releasing the first occluding disk 201 which is relatively far away from the delivery device 50 in the left atrium until the first occluding disk 201 is unfolded in the left atrium;

S22. then, withdrawing the delivery sheath and the delivery device 50 together, and S23. when the delivery sheath is withdrawn to the inside of the right atrium, releasing the second occluding disk 205 until the second occluding disk 205 is unfolded in the right atrium; at the moment, the knot 22 is in an untightened state, all of the base thread loop 221, the locking thread loop 223 and the adjusting thread loop 230 are in the untightened state, and all the thread loops are not tightened.

According to the present disclosure, the method of occluding an oval foramen further includes:

S3. adjusting the length of the tightening thread between the first occluding disk and the second occluding disk such that tissues surrounding the oval foramen is clamped by the first occluding disk and the second occluding disk.

The step S3 may specifically include: pulling the free end of the adjusting section 25 by the delivery device 50 towards the proximal end to reduce the length of the adjusting thread loop 230, thereby reducing the length of the tightening thread 21 between the first occluding disk 201 and the second occluding disk 205 and driving the first occluding disk 201 and the second occluding disk 205 to move relative to the atrial septum until the inner side of the first occluding disk 201 is attached to one side of the atrial septum surrounding the oval foramen 200 and the inner side of the second occluding disk 205 is attached to the other end of the atrial septum surrounding the oval foramen 200.

In some embodiments, the method of occluding an oval foramen may further include:

S4. fixing the length of the tightening thread between the first occluding disk and the second occluding disk after adjusting the length of the tightening thread between the first occluding disk and the second occluding disk.

The step S4 may specifically include:

when the atrial septum surrounding the oval foramen 200 is firmly clamped by the first occluding disk 201 and the second occluding disk 205, pulling the free end of the locking section 24 to the proximal end by the delivery device 50 to gradually tighten the locking thread loop 223, driving the base thread loop 221 to be locked after the locking thread loop 223 is tightened, and finally, tightening both of the locking thread loop 223 and the base thread loop 221, so that the end of the adjusting thread loop 230 connected with the adjusting section 25 is tightened and locked by the locking thread loop 223 and is fixed between the locking thread loop 223 and the base thread loop 221, that is, the adjusting thread loop 230 is locked by the base thread loop 221 and the locking thread loop 223 together, the length of the adjusting thread loop 230 between the first occluding disk 201 and the second occluding disk 205 is fixed, and thus, the atrial septum is clamped by the first occluding disk 201 and the second occluding disk 205.

In some embodiments, the method of occluding an oval foramen may further include:

S5. after knotting is completed, pushing a thread cutter to the right atrium through the delivery sheath, cutting the thread off on a position 3 to 5 mm away from the knot, and withdrawing the delivery sheath and the thread cutter, and thus, the occlusion of the oval foramen 200 is completed.

Figure 16:
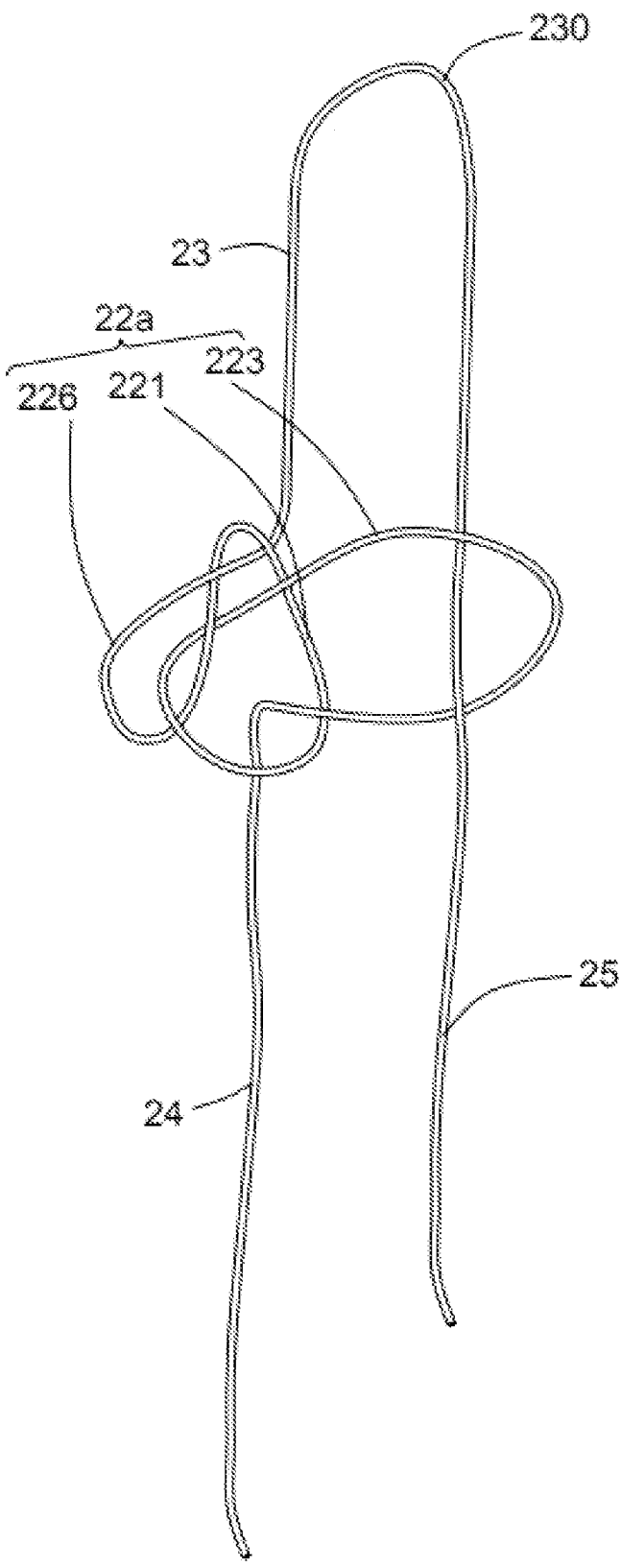
FIG. 16 is a schematic structural view of a tightening element of an occluder according to a second embodiment of the present disclosure.

Reference is made to FIG. 16, an occluder provided in a second embodiment of the present disclosure has a structure after release similar to that of the first embodiment, except that a knot 22a of a tightening thread 21a of the occluder in the second embodiment has a structure slightly different from the structure of the knot 22 in the first embodiment. The knot 22a is additionally provided with a reinforcing thread loop 226 on the basis of the knot 22 in the first embodiment. One end of the reinforcing thread loop 226 is connected to the base thread loop 221, and the other end of the reinforcing thread loop 226 passes through a gap between the base thread loop 221 and the locking thread loop 223 to connect with the adjusting thread loop 230. After the locking section 24 is tightened, in a process that the base thread loop 221 and the locking thread loop 223 are tightened, in addition to the adjusting section 25 being tightened by the locking thread loop 223, two ends of the reinforcing thread loop 226 are further tightened by the base thread loop 221, and thus, the capability of the locking thread loop 223 locking the adjusting section 25 is improved.

Figure 17:
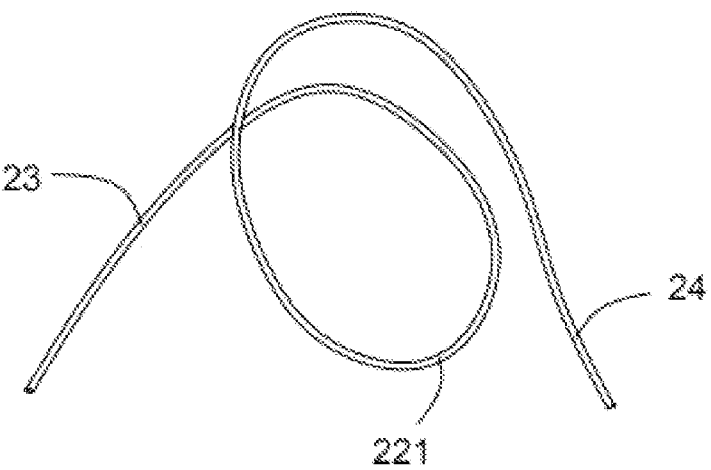
FIG. 17 is a schematic view illustrating a procedure of a knotting process of a tightening thread of the occluder according the second embodiment of the present disclosure.
Figure 18:
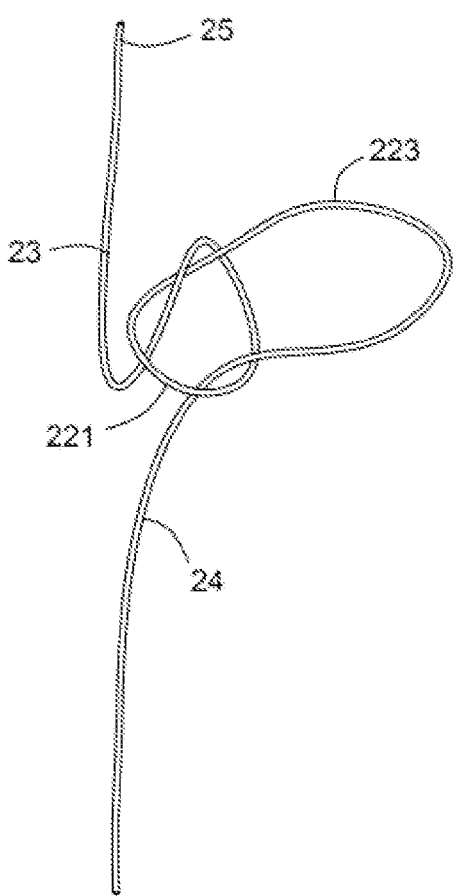
FIG. 18 is a schematic view illustrating another procedure of a knotting process of a tightening thread of the occluder according the second embodiment of the present disclosure.
Figure 19:
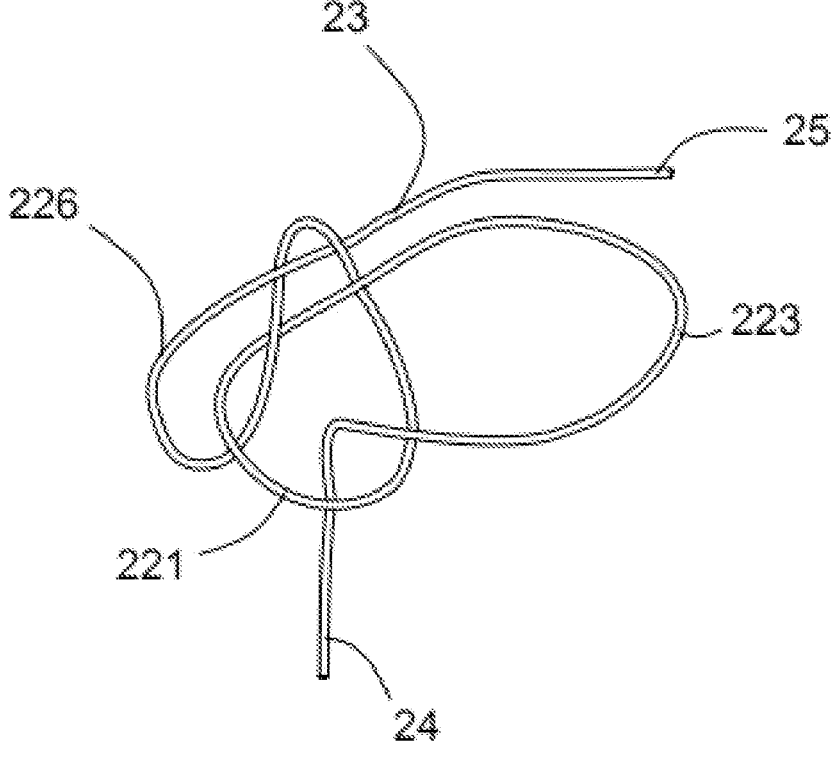
FIG. 19 is a schematic view illustrating another procedure of a knotting process of a tightening thread of the occluder according the second embodiment of the present disclosure.

As shown in FIG. 17 to FIG. 19, a knotting method of the knot 22a is similar to the knotting method of the knot 22, which is specifically described as follows.

Figure 20:
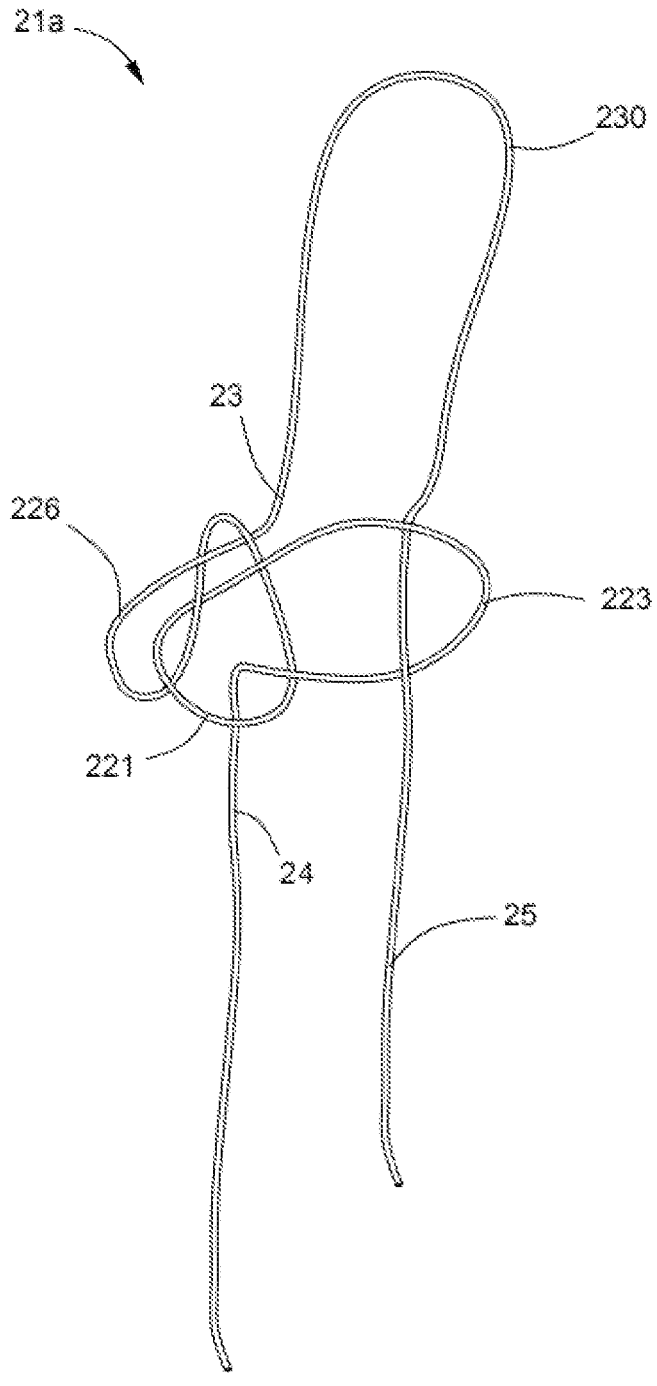
FIG. 20 is a schematic view illustrating another procedure of a knotting process of a tightening thread of the occluder according the second embodiment of the present disclosure.

1. as shown in FIG. 17, forming a thread loop by overlapping two ends of the first section of the thread body, thereby obtaining the base thread loop 221;

2. as shown in FIG. 18, directing a remaining part of the first section other than the base thread loop 221 to pass through the base thread loop 221, to thereby obtain a U-shaped locking thread loop 223;

3. as shown in FIG. 19, directing the adjusting section 25 to pass through a gap between the base thread loop 221 and the locking thread loop 223 in a first direction to obtain the reinforcing thread loop 226; and 4. as shown in FIG. 20, directing the adjusting section 25 to pass through the locking thread loop 223 in a second direction opposite to the first direction such that the adjusting thread loop 230 is defined by the part of the thread body between the base thread loop 221 and the locking thread loop 223, thereby obtaining the tightening thread 21*a*.

The base thread loop 221 and the locking thread loop 223 of the tightening thread 21*a* partially overlap, and the first direction and the second direction may be defined as one of the two situations described as follows.

1. the first direction refers to a direction from the locking thread loop 223 towards the base thread loop 221, for example, an inward direction perpendicular to the plane where FIG. 19 locates.

2. the first direction refers to a direction from the base thread loop 221 towards the locking thread loop 223, for example, an outward direction perpendicular to the plane where FIG. 19 locates.

A method for assembling the tightening thread 21*a* with the first occluding disk 201 and the second occluding disk 205 in the second embodiment is similar to that in the first embodiment, that is, before the knot 22*a* is knotted, directing one end of the thread body to pass through the mesh openings of the first occluding disk 201 first, then to return to the inner side of the first occluding disk 201 adjacent to the other end of the thread body, so that the thread body is located on the inner side of the first occluding disk 201; then, directing one end of the t thread body to pass through the threading hole 2056 of the second rigid sleeve 2055 from the inner side to the outer side of the second occluding disk 205, and directing the other end of the thread body to pass through a mesh opening adjacent to the second rigid sleeve 2055 from the inner side to the outer side of the second occluding disk 205, so that the two ends of the thread body are located side by side on the outer side of the second occluding disk 205, and the part of the thread body located between the first occluding disk 201 and the second occluding disk 205 forms the adjusting thread loop 230; and then, a knotting method for the knot 22*a* is preformed.

A using process of an occluding system of the second embodiment is the same as the using process of the occluding system of the first embodiment, which will not be described again.

In other modified implementations, the locking section 24 and the adjusting section 25 may also be inserted into and wound around the adjusting thread loop 230 and the locking ring thread 223 several more times, provided that length adjustment and locking functions are not impeded.

In other modified implementations, the knot 22 may be further knotted in other manners, as long as the knot 22 is coupled with the first occluding disk 201 or the second occluding disk 205, which can adjust the length of the connecting section 23 and can be locked.

In other modified implementations, the first rigid sleeve 2015 and the second rigid sleeve 2055 are omitted in the first occluding disk 201 and the second occluding disk 205, and the tightening thread 21 passes through the mesh openings of the first occluding disk 201 and the second occluding disk 205 so as to be connected with the first occluding disk 201 and the second occluding disk 205.

In other modified implementations, each of the first occluding disk 201 and the second occluding disk 205 may be a single-layer meshed disk or a double-layer meshed disk.

In other modified implementations, a gasket is additionally provided on the basis of the first embodiment. Specifically, the gasket is disposed on the geometric center of the outer side of the second occluding disk 205. The gasket is provided with through holes extending in the thickness direction of the second occluding disk 205 which are spaced apart. As shown in FIG. 2, one of the through holes corresponds to the threading hole 2056 of the second rigid sleeve 2055 for one end of the adjusting thread loop 230 passing through. The other through hole corresponds to the other end of the adjusting thread loop 230 for the other end of the adjusting thread loop 230 passing through. All of the knot 22, the locking section 24 and the adjusting section 25 are located on the side of the gasket away from the second occluding disk 205. In the present embodiment, by using the gasket, force applied on the outer side of the second occluding disk 205 is more uniform, so that a clamping force between the first occluding disk 201 and the second occluding disk 205 is more uniform to achieve more stable occlusion.

For the convenience of description, serial numbers have been used in all the steps of the above-mentioned method. It should be noted that the above-mentioned serial numbers are not used for limiting an order relationship among the steps. The specific technical solution in each of the above-mentioned embodiments may be applicable to each other without departing from the spirit of the present disclosure.

The above descriptions are implementations of the embodiments of the present disclosure. It should be noted that those of ordinary skill in the art may also make several improvements and modifications without departing from the principles of the embodiments of the present disclosure, and these improvements and modifications are also considered to fall within the protection scope of the present disclosure.

What is claimed is:

1. An occluder for occluding a defect in a vasculature, wherein the occluder comprises:

a first occluding disk and a second occluding disk, configured for covering different openings of the defect; and a tightening element comprising a tightening thread, the tightening thread passing through the defect and being connected to the two occluding disks, wherein the tightening thread has a length between the two occluding disks, and a distance between the two occluding disks is adjustable by adjusting the length of the tightening thread;

wherein the tightening thread comprises:

a knot;

a connecting section connected with the knot, and connected between the first occluding disk and the second occluding disk, the connecting section having a length; and a locking section and an adjusting section each being connected with the knot and each comprising a free end;

wherein all of the locking section, the adjusting section and the knot are disposed on a side of the second occluding disk away from the first occluding disk;

the length of the tightening thread between the two occluding disks is adjustable by adjusting the length of the connecting section through operating the free end of the adjusting section;

the adjusting section is lockable by the knot by pulling the free end of the locking section, thereby fixing the distance between the two occluding disks;

wherein the locking section and the adjusting section are operable independently through their respective free ends; and wherein the tightening element further comprises a fixing thread connected with a delivery device, and one of the two occluding disks is fixed to a distal end of the delivery device by means of the fixing thread.

2. The occluder according to claim 1, wherein the connecting section is connected to the geometric center of the first occluding disk, and/or the connecting section is connected to the geometric center of the second occluding disk.

3. The occluder according to claim 1, wherein the connecting section is an adjusting thread loop defined by the tightening thread, two ends of the adjusting thread loop pass through the second occluding disk and are connected with the knot, and a part of the adjusting thread loop away from the knot passes through the first occluding disk.

4. The occluder according to claim 3, wherein one end of the adjusting thread loop passes through the knot and is connected with the adjusting section;

when the knot is not tightened, the adjusting section is capable of driving the end of the adjusting thread loop connected with the adjusting section to slide in the knot to adjust the length of the adjusting thread loop between the first occluding disk and the second occluding disk; and the locking section is configured for tightening the knot to make the knot tighten a part of the adjusting thread loop located in the knot, so as to fix the length of the adjusting thread loop between the first occluding disk and the second occluding disk.

5. The occluder according to claim 4, wherein the knot comprises a base thread loop and a locking thread loop which are interconnected, one end of the adjusting thread loop is connected with the base thread loop, and the other end of the adjusting thread loop passes through the locking thread loop and is connected with the adjusting section;

when the base thread loop and the locking thread loop are not tightened, the adjusting section is capable of driving the end of the adjusting thread loop connected with the adjusting section to slide in the locking thread loop to adjust the length of the adjusting thread loop between the first occluding disk and the second occluding disk; and the locking section is pulled to make the locking thread loop and the base thread loop be sequentially and gradually tightened so that the part of the adjusting thread loop is tightened and locked in the locking thread loop.

6. The occluder according to claim 5, wherein the tightening thread comprises a first section connected with the locking section and a second section connected with the adjusting section, and the first section and the second section are interconnected;

the base thread loop is defined by the first section, and the locking thread loop is formed by a remaining part of the first section passing through the base thread loop; and the adjusting thread loop is defined by the second section.

7. The occluder according to claim 5, wherein the knot further comprises a reinforcing thread loop, and one end of the reinforcing thread loop is connected to the base thread loop, and an other end of the reinforcing thread loop passes through a gap between the base thread loop and the locking thread loop and is connected with the adjusting thread loop.

8. The occluder according to claim 3, wherein the first occluding disk comprises a first supporting frame and a first flow blocking membrane disposed on the first supporting frame, and the tightening thread is connected with the first supporting frame and/or the first flow blocking membrane.

9. The occluder according to claim 8, wherein the second occluding disk comprises a second supporting frame and a second flow blocking membrane disposed on the second supporting frame, and one end of the adjusting thread loop passes through the second flow blocking membrane from a gap in the second supporting frame, so as to be connected with the knot.

10. The occluder according to claim 9, wherein the second occluding disk further comprises a rigid sleeve, the rigid sleeve is connected with the second supporting frame, the rigid sleeve is provided with a through threading hole in a thickness direction of the second supporting frame, and the other end of the adjusting thread loop passes through the threading hole so as to be connected with the knot.

11. The occluder according to claim 9, wherein the first supporting frame and the second supporting frame are woven meshed structures or cut frame structures; and wherein each of the first supporting frame and the second supporting frame is any one of the following: a single-layer woven meshed structure, a single-layer cut frame structure, a double-layer meshed structure or a double-layer cut frame structure.

12. The occluder according to claim 9, wherein a peripheral edge of the first supporting frame is inclinedly bent towards the second supporting frame, and a peripheral edge of the second supporting frame is inclinedly bent towards the first supporting frame.

13. The occluder according to claim 9, wherein at least one of the first supporting frame and the second supporting frame comprises a plurality of supporting wire units which are arranged in an annular array.

14. A method of occluding an oval foramen in a heart of a patient with the occluder according to claim 3, wherein one end of the adjusting thread loop passes through the knot and is connected with the adjusting section, the method comprising steps of:

delivering the occluder into the heart of the patient;

releasing the first occluding disk into a left atrium of the heart, and releasing the second occluding disk into a right atrium, with the tightening thread passing through the oval foramen;

adjusting the length of the tightening thread between the first occluding disk and the second occluding disk by driving the end of the adjusting section connected with the adjusting loop to slide in the knot when the knot is not tightened, such that tissues surrounding the oval foramen are clamped by the first occluding disk and the second occluding disk; and fixing the length of the adjusting thread loop between the first occluding disk and the second occluding disk by driving the end of the locking section to tighten the knot, such that the knot tightens a part of the adjusting thread loop located in the knot.

15. The occluder according to claim 1, wherein the tightening thread is an absorbable biocompatible suture.

16. An occluding system, comprising the occluder according to claim 1, wherein the system further comprises a delivery device, and the delivery device is used for releasing the occluder.

17. A knotting method for a tightening element of the occlude according to claim 1, wherein the tightening thread is formed by twisting and knotting a thread body, the thread body comprises a locking section, a first section, a second section and an adjusting section which are connected in sequence, and the knotting method comprises the following steps:

forming a thread loop by the first section to obtain a base thread loop;

directing a remaining part of the first section to pass through the base thread loop to obtain a locking thread loop; and directing the adjusting section to pass through the locking thread loop such that the second section forms an adjusting thread loop between two occluding disks of the occluder, thereby obtaining the tightening thread.

18. The knotting method for the tightening element of the occluder according to claim 17, wherein between the step of "directing a remaining part of the first section to pass through the base thread loop to obtain a locking thread loop" and the step of "directing the adjusting section to pass through the locking thread loop such that the second section forms an adjusting thread loop between two occluding disks of the occluder, thereby obtaining the tightening thread", the knotting method further comprises:

directing the adjusting section to pass through a gap between the base thread loop and the locking thread loop in a first direction to obtain a reinforcing thread loop; and wherein the step of "directing the adjusting section to pass through the locking thread loop such that the second section forms an adjusting thread loop between two occluding disks of the occluder, thereby obtaining the tightening thread" specifically comprises:

directing the adjusting section to pass through the locking thread loop in a second direction opposite to the first direction such that the second section forms the adjusting thread loop between the two occluding disks of the occluder, thereby obtaining the tightening element; wherein the first direction refers to a direction from the locking thread loop towards the base thread loop; or the first direction refers to a direction from the base thread loop to the locking thread loop.

19. A method of occluding an oval foramen in a heart of a patient with the occluder according to claim 1, wherein the method comprising steps of:

delivering the occluder into the heart of the patient;

releasing the first occluding disk into a left atrium of the heart, and releasing the second occluding disk into a right atrium, with the tightening thread passing through the oval foramen; and adjusting the length of the tightening thread between the first occluding disk and the second occluding disk such that tissues surrounding the oval foramen are clamped by the first occluding disk and the second occluding disk.

20. The method of occluding an oval foramen in a heart of a patient according to claim 19, further comprising a step of fixing the length of the tightening thread between the first occluding disk and the second occluding disk after adjusting the length of the tightening thread between the first occluding disk and the second occluding disk.

21. The method of occluding an oval foramen in a heart of a patient according to claim 20, wherein the tightening thread comprises an additional free end; and wherein the step of fixing the length of the tightening thread between the first occluding disk and the second occluding disk comprises driving the additional free end of the tightening thread.

22. The method of occluding an oval foramen in a heart of a patient according to claim 19, wherein the step of adjusting the length of the tightening thread between the first occluding disk and the second occluding disk comprises driving the free end of the tightening thread.

23. A knotting method for a tightening element of an occlude comprising:

two occluding disks, configured for covering different openings of the defect; and a tightening element comprising a tightening thread, the tightening thread passing through the defect and being connected to the two occluding disks, wherein the tightening thread has a length between the two occluding disks, and the length is adjustable by means of a free end of the tightening thread; and wherein the tightening thread is formed by twisting and knotting a thread body, the thread body comprises a locking section, a first section, a second section and an adjusting section which are connected in sequence, the knotting method comprises the following steps:

forming a thread loop by the first section to obtain a base thread loop;

directing a remaining part of the first section to pass through the base thread loop to obtain a locking thread loop;

directing the adjusting section to pass through a gap between the base thread loop and the locking thread loop in a first direction to obtain a reinforcing thread loop; and directing the adjusting section to pass through the locking thread loop such that the second section forms an adjusting thread loop between two occluding disks of the occluder, thereby obtaining the tightening thread, wherein the step of "directing the adjusting section to pass through the locking thread loop such that the second section forms an adjusting thread loop between two occluding disks of the occluder, thereby obtaining the tightening thread" specifically comprises:

directing the adjusting section to pass through the locking thread loop in a second direction opposite to the first direction such that the second section forms the adjusting thread loop between the two occluding disks of the occluder, thereby obtaining the tightening element; wherein the first direction refers to a direction from the locking thread loop towards the base thread loop; or the first direction refers to a direction from the base thread loop to the locking thread loop.

24. A method of occluding an oval foramen in a heart of a patient with an occlude comprising:

two occluding disks, configured for covering different openings of the defect; and a tightening element comprising a tightening thread, the tightening thread passing through the defect and being connected to the two occluding disks, wherein the tightening thread has a length between the two occluding disks, and the length is adjustable by means of a free end of the tightening thread;

wherein the two occluding disks comprise a first occluding disk and a second occluding disk, the method comprising steps of:

delivering the occluder into the heart of the patient;

releasing the first occluding disk into a left atrium of the heart, and releasing the second occluding disk into a right atrium, with the tightening thread passing through the oval foramen;

adjusting the length of the tightening thread between the first occluding disk and the second occluding disk such that tissues surrounding the oval foramen are clamped by the first occluding disk and the second occluding disk; and fixing the length of the tightening thread between the first occluding disk and the second occluding disk after adjusting the length of the tightening thread between the first occluding disk and the second occluding disk, wherein the tightening thread comprises an additional free end; and wherein the step of fixing the length of the tightening thread between the first occluding disk and the second occluding disk comprises driving the additional free end of the tightening thread.

* * * * *